US012560594B2

(12) United States Patent
Kang et al.

(10) Patent No.: US 12,560,594 B2
(45) Date of Patent: Feb. 24, 2026

(54) CDR ANTIBODY REACTION APPARATUS

(71) Applicants: T-MAC CO., LTD., Daejeon (KR);
Korea Research Institute of
Bioscience and Biotechnology,
Daejeon (KR)

(72) Inventors: Sung Hyun Kang, Daejeon (KR); Jong
Taek Park, Daejeon (KR); You Rim
Cha, Daejeon (KR); Woo Jong Ha,
Sejong-si (KR); Heung Seon Shin,
Sejong-si (KR)

(73) Assignees: T-MAC CO., LTD., Daejeon (KR);
Korea Research Institute of
Bioscience and Biotechnology,
Daejeon (KR)

( * ) Notice: Subject to any disclaimer, the term of this
patent is extended or adjusted under 35
U.S.C. 154(b) by 684 days.

(21) Appl. No.: 17/918,530

(22) PCT Filed: Nov. 8, 2021

(86) PCT No.: PCT/KR2021/016159
§ 371 (c)(1),
(2) Date: Oct. 12, 2022

(87) PCT Pub. No.: WO2022/114597
PCT Pub. Date: Jun. 2, 2022

(65) Prior Publication Data
US 2023/0204566 A1     Jun. 29, 2023

(30) Foreign Application Priority Data
Nov. 25, 2020    (KR) ........................ 10-2020-0160092

(51) Int. Cl.
*G01N 33/53*         (2006.01)
(52) U.S. Cl.
CPC ............................... *G01N 33/5304* (2013.01)
(58) Field of Classification Search
None
See application file for complete search history.

(56) References Cited

U.S. PATENT DOCUMENTS

| | | | | | |
|---|---|---|---|---|---|
| 4,810,348 | A | * | 3/1989 | Sarrine ............ | G01N 27/44721 |
| | | | | | 204/612 |
| 5,776,684 | A | * | 7/1998 | Chirikjian ............ | C12Q 1/6816 |
| | | | | | 435/6.15 |
| 2013/0213811 | A1 | * | 8/2013 | Kennedy .......... | G01N 27/44739 |
| | | | | | 204/601 |
| 2019/0064140 | A1 | * | 2/2019 | Lee .................. | G01N 35/00029 |

FOREIGN PATENT DOCUMENTS

| | | | | | |
|---|---|---|---|---|---|
| JP | 2011058968 | * | 3/2011 | .......... | G01N 27/447 |
| JP | 2011058968 | A | 3/2011 | | |
| KR | 101689445 | * | 12/2016 | | |
| KR | 101689445 | B1 | 12/2016 | | |
| KR | 20170073529 | * | 6/2017 | .......... | G01N 27/447 |
| KR | 20170073529 | A | 6/2017 | | |
| KR | 20190005054 | A | 1/2019 | | |
| KR | 102227520 | * | 3/2021 | ............... | B01L 3/60 |
| KR | 102227520 | B1 | 3/2021 | | |

OTHER PUBLICATIONS

Sanchez et al., "Molecular Detection and Typing," Methods in Molecular Biology, vol. 268, 2004, 12 pages.
Sunman et al., "Reversal of the Transformed Phenotype and Inhibition of Peptidylglycine Monooxygenase in Ras-Transformed Cells by 4-Phenyl-3-Butenoic Acid," Molecular Carcinogenesis, 2004, 16 pages.
International Search Report and Written Opinion for Application No. PCT/KR2021/016159, mailed Feb. 15, 2022, 10 pages.
Sajjad et al., "Rapid and Efficient Western Blot Assay by Rotational Cyclic Draining and Replenishing Procedure," Electrophoresis, 2018, 5 pages.

* cited by examiner

*Primary Examiner* — Ann Montgomery
(74) *Attorney, Agent, or Firm* — Barry L. Davison; Davis Wright Tremaine LLP

(57) ABSTRACT

A cyclic draining and replenishing (CDR) antibody reaction apparatus according to the present invention comprises: a chamber part inside which an antibody solution is accommodated, and in which a blotting membrane that reacts with the antibody solution is arranged; and a spreader arranged on the blotting membrane in the chamber part, wherein the position of the spreader moves along the top of the blotting membrane.

9 Claims, 13 Drawing Sheets

【Figure 1】
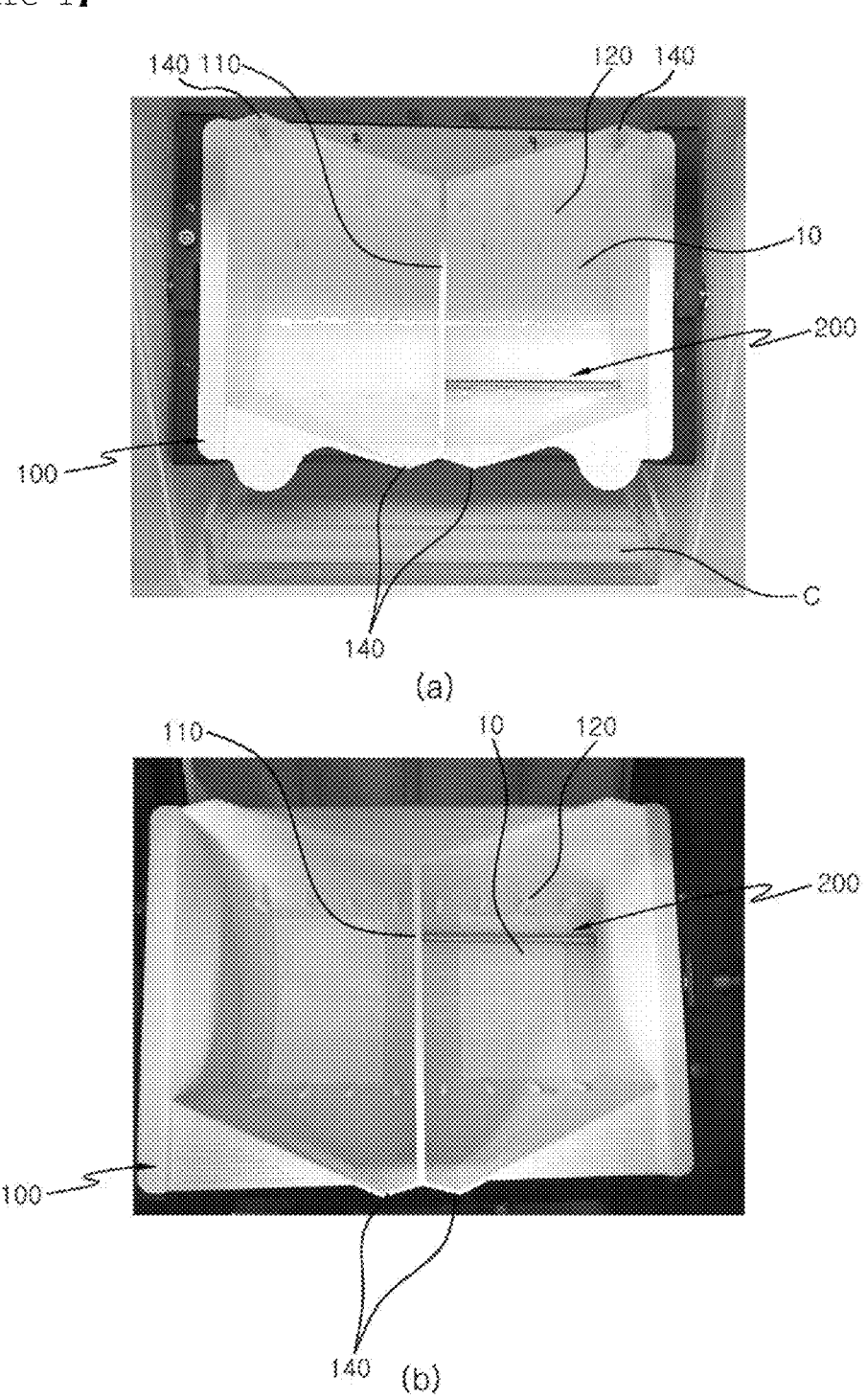
(a)
(b)

【Figure 2】
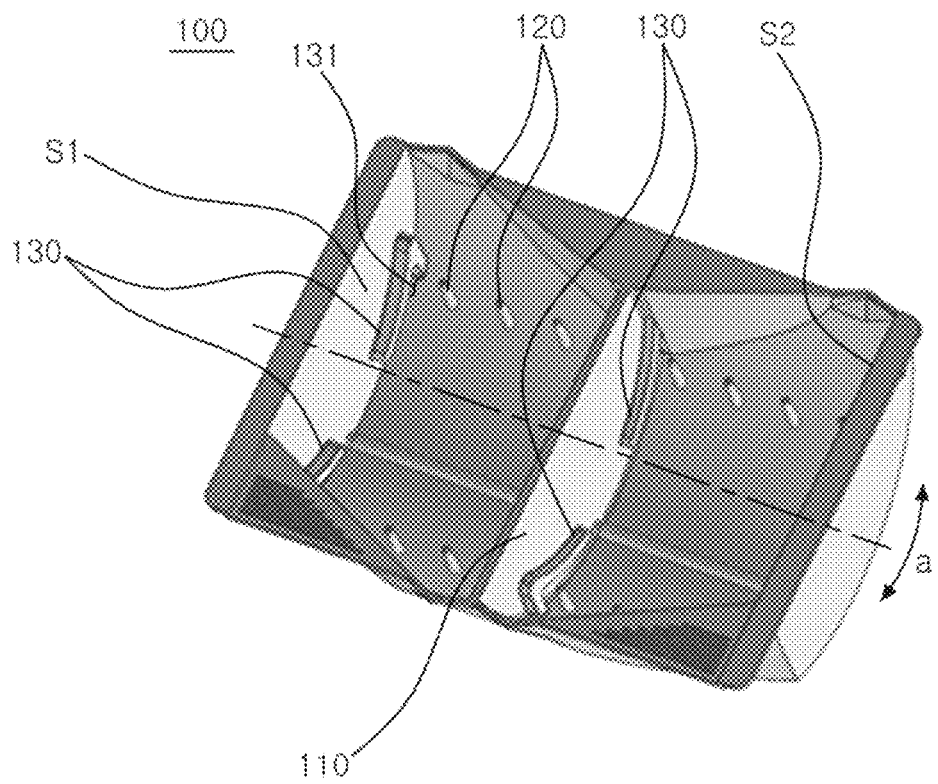

【Figure 3】
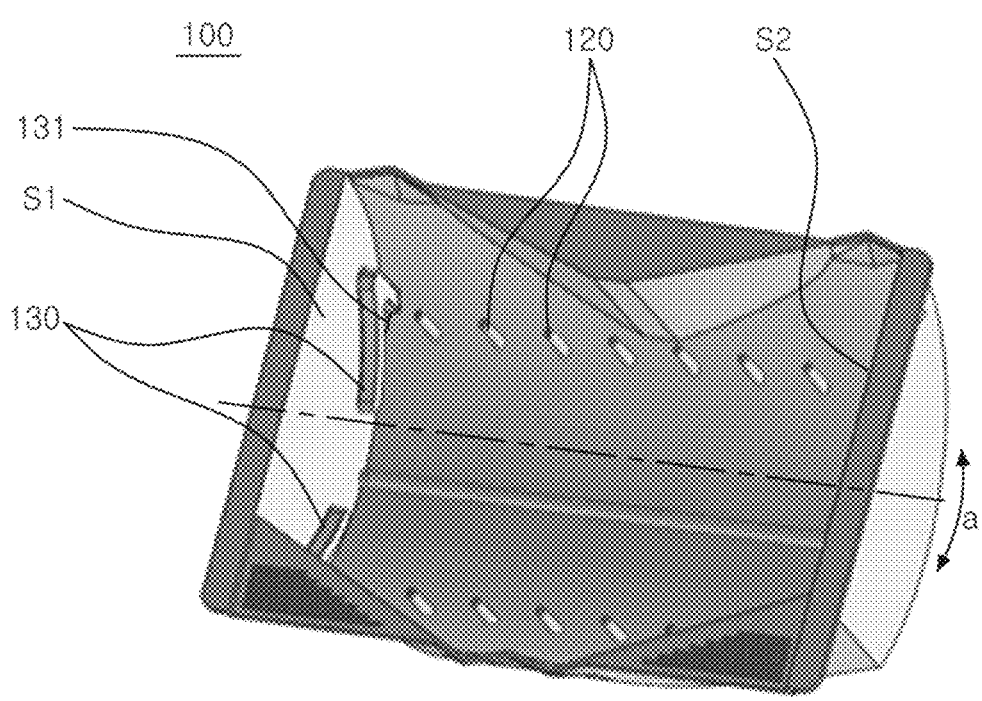

[Figure 4]
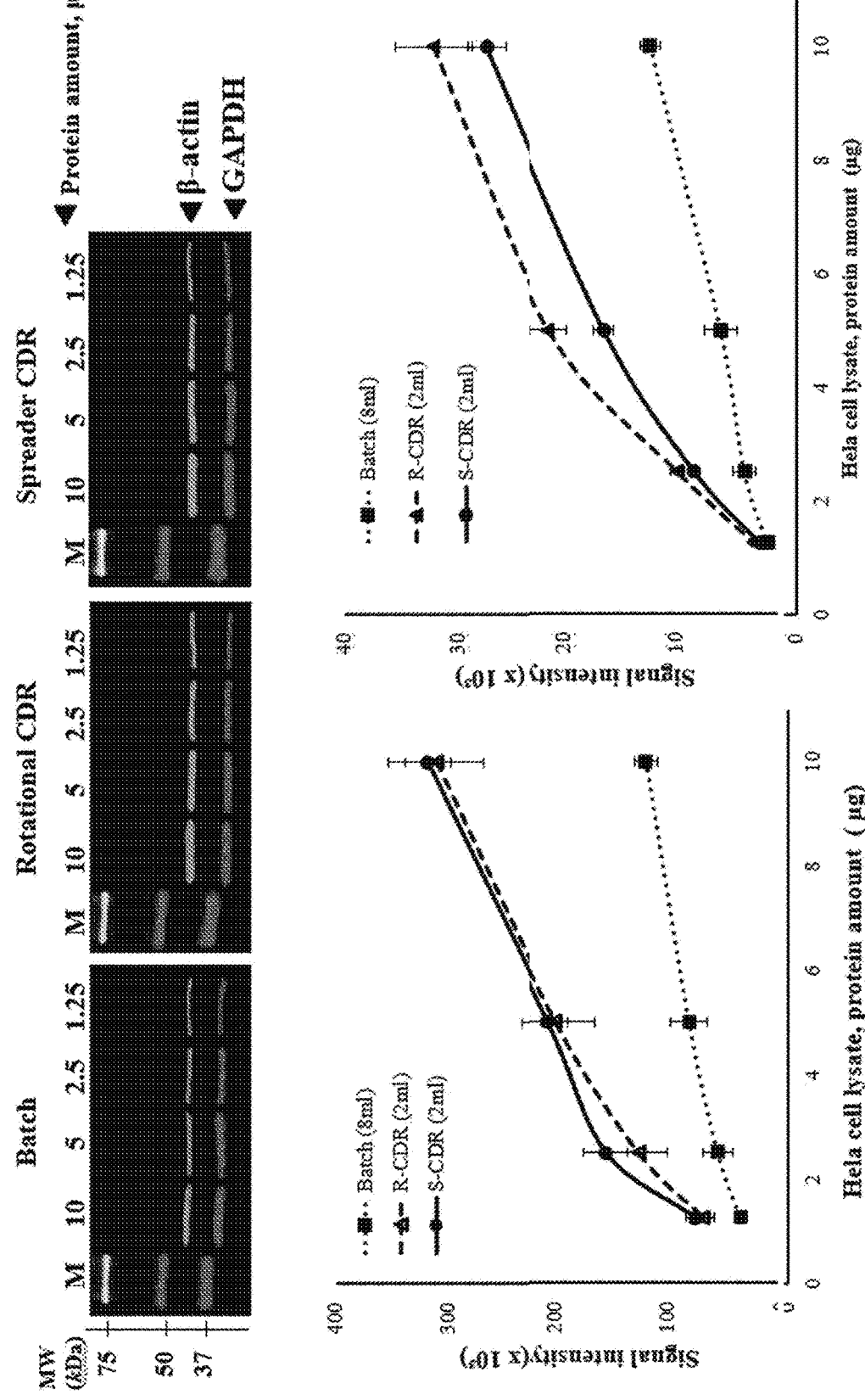

[Figure 5]
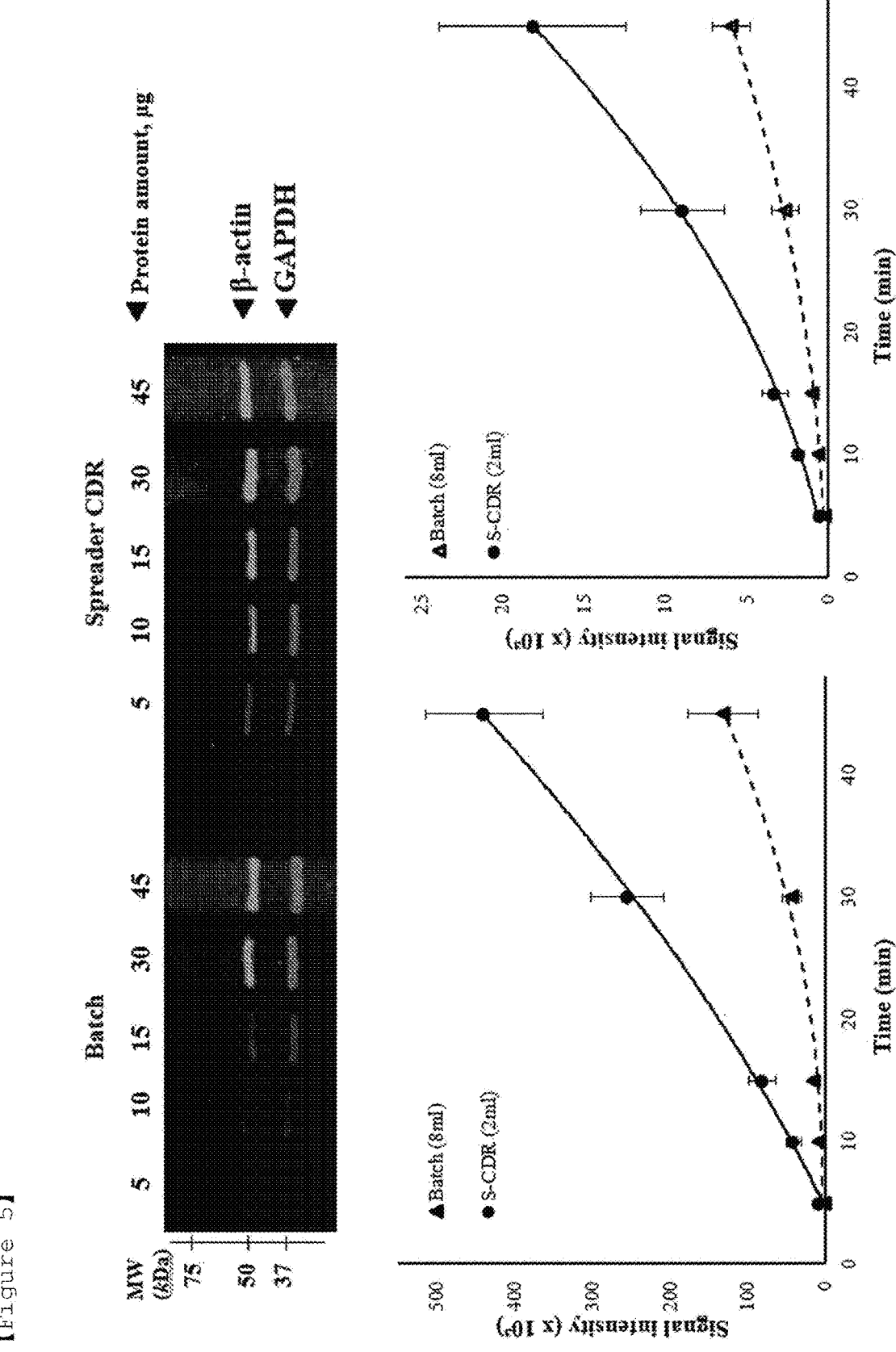

【Figure 6】
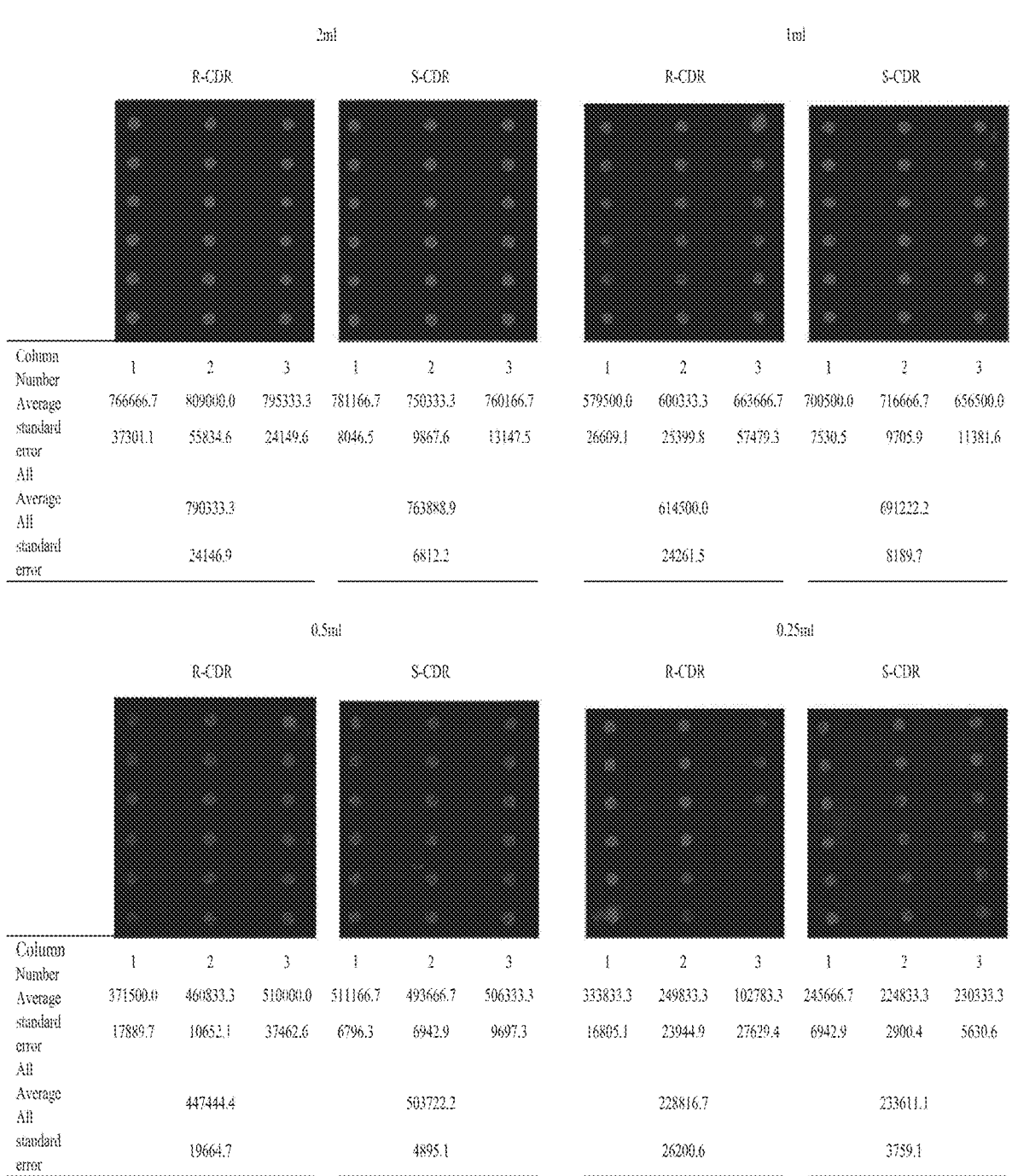

【Figure 7a】
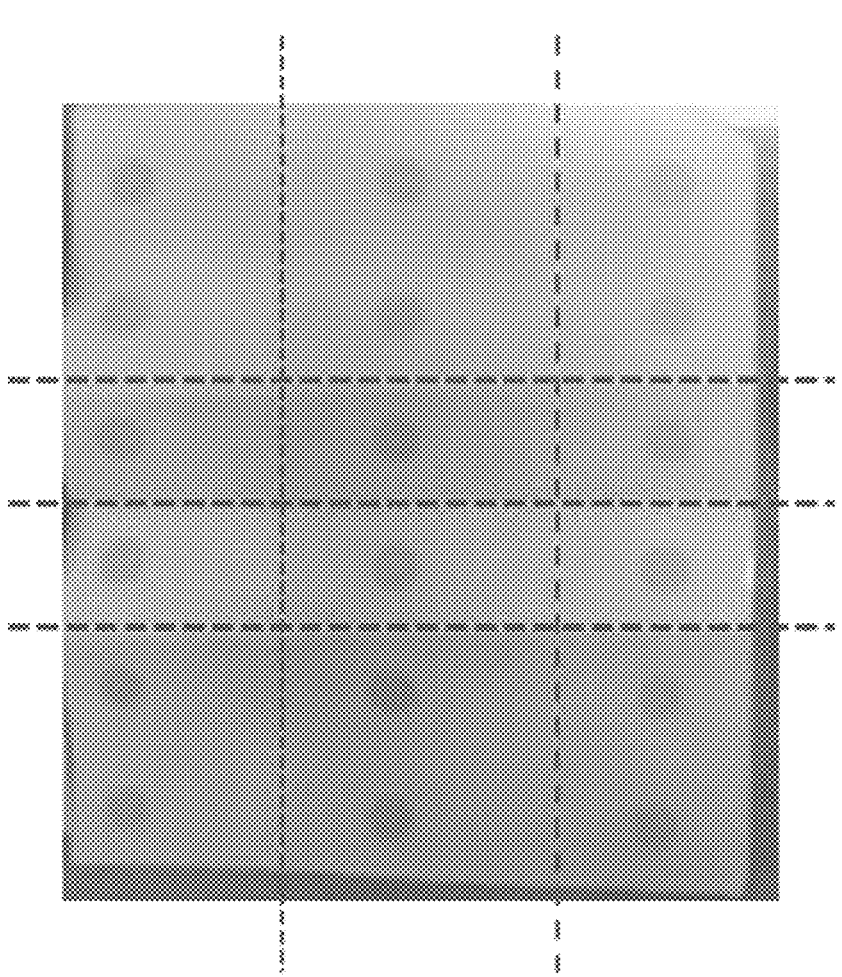
- - - - - - FOLDING INWARD

[Figure 7b]

【Figure 8】
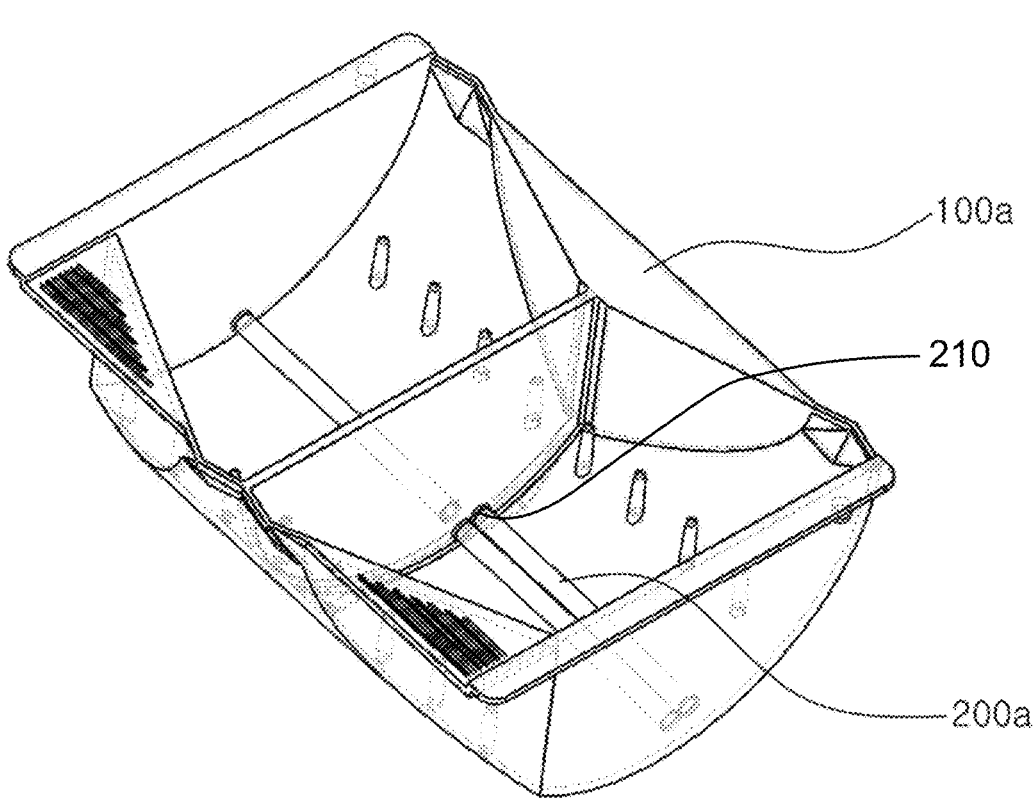

【Figure 9】
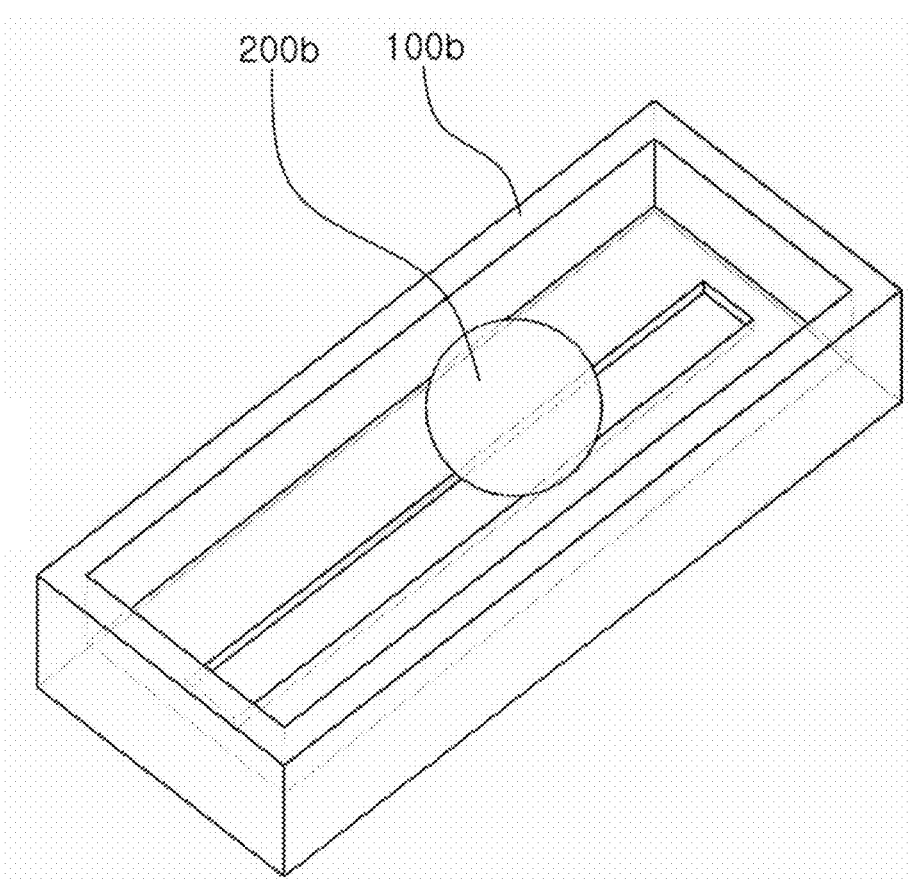

【Figure 10】
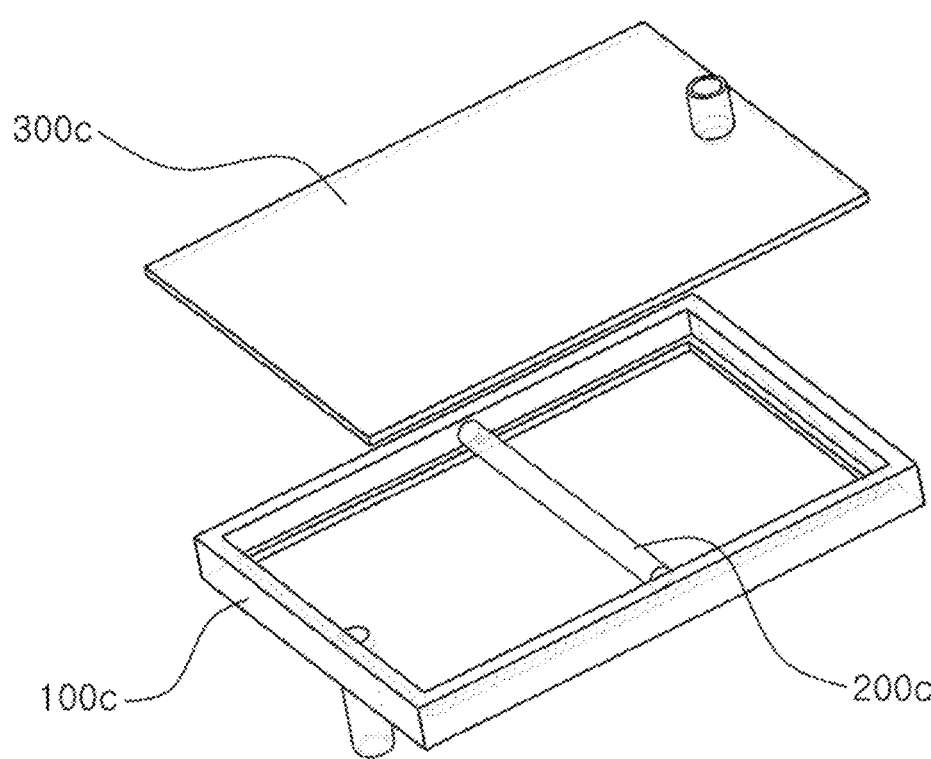

【Figure 11】
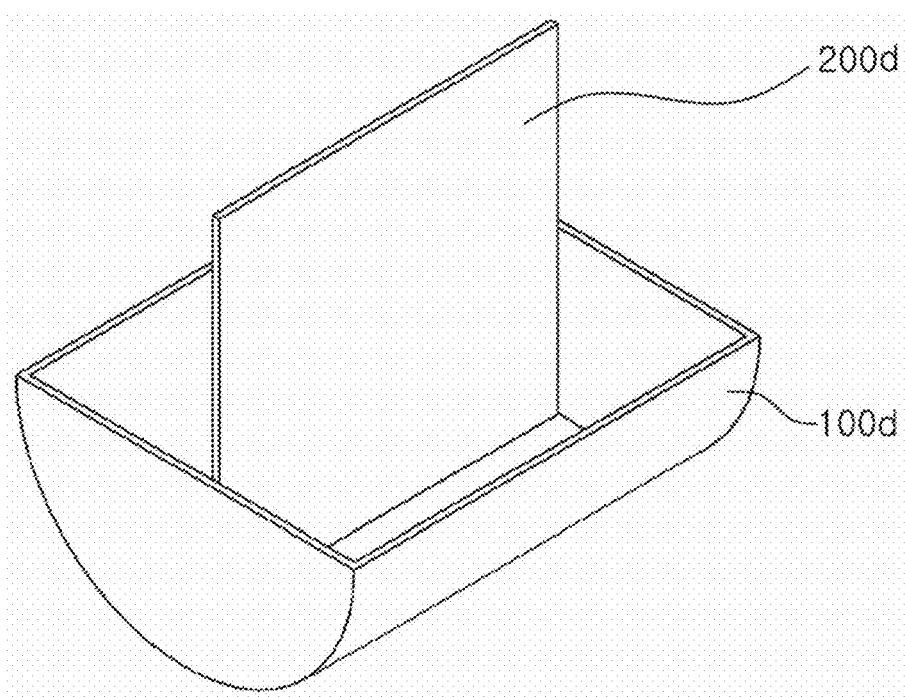

【Figure 12】
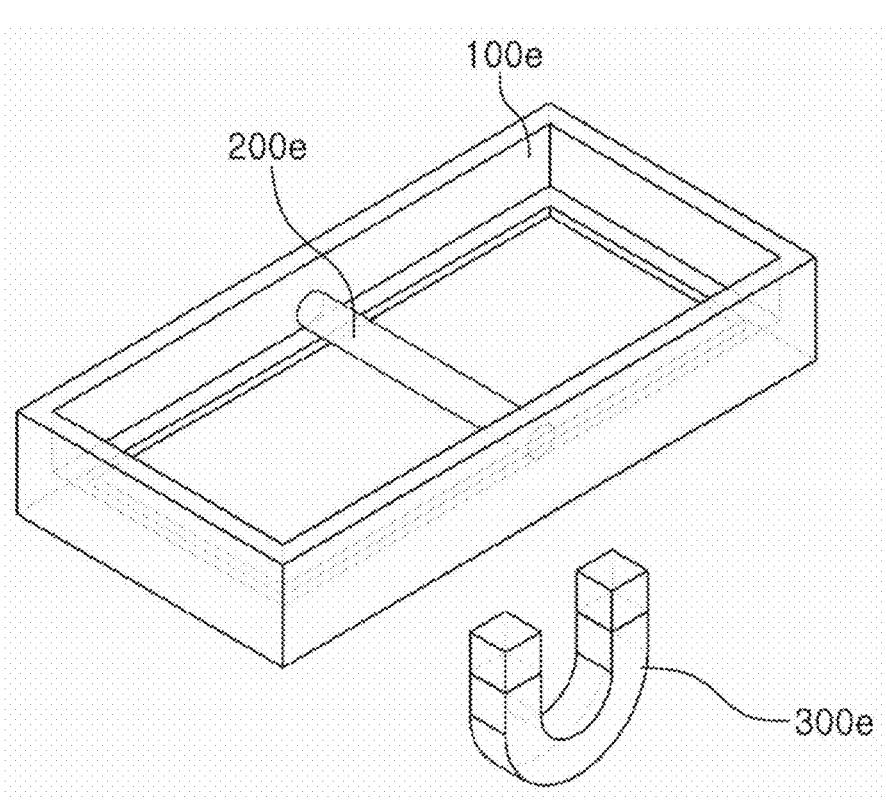

CDR ANTIBODY REACTION APPARATUS

TECHNICAL FIELD

The present invention relates to an antibody reaction apparatus to which the principle of cyclic draining and replenishing (CDR) is applied, and more particularly, to a CDR antibody reaction apparatus which allows blotting even with a small amount of antibody solution, allows a uniform antibody reaction to occur regardless of the membrane size, the placement direction of membrane, and the relative position within a membrane, and improves the antigen binging efficacy compared to conventional bath methods.

BACKGROUND ART

Western blot, also known as protein blot or immunoblot, is a major technique for detecting specific proteins in the fields of molecular biology and biochemistry.

The Western blot process generally involves the separation of proteins based on their size by gel electrophoresis, the transfer of proteins to a nitrocellulose or PVDF transfer membrane, the treatment of an antibody against a target protein, and the detection of the target protein through antibody labelling.

Here, the process of reacting an antigen-immobilized membrane (nitrocellulose, PVDF, etc.) in an antibody solution for the binding of the antibody to its target protein is the most time-consuming step and determines the processing time of the Western blot.

Conventionally, to perform the antibody reaction to occur as described above, the membrane is placed in a vessel with an antibody solution in an amount sufficient to cover the membrane and then stirred to facilitate the antibody reaction.

Meanwhile, CDR (cyclic draining and replenishing) method is performed by repeating the process of adding and removing the antibody solution to and from the membrane, and according to several studies, the CDR method has the advantages of reducing the antibody reaction time, improving sensitivity, and exhibiting high antibody binding efficiency even with a low concentration antibody solution, compared to conventional methods.

In an R-CDR (rotational CDR) reaction vessel to which this CDR method is applied, the amount of antibody solution is given enough to cover the lower part of the reaction vessel, resulting in a reduced amount of antibody solution, compared to conventional methods in which the membrane is fully immersed in a plastic vessel such as a business card case.

The reaction vessel used in the conventional R-CDR method is provided with a rotating cylindrical tube, and for each step, it is necessary that the cylindrical reaction vessel be removed from the rotating device and the lid be opened to add or remove a solution, which complicates the use of the reaction vessel.

Moreover, if the amount of antibody solution is very small, the antibody solution does not flow evenly in the rotating reaction vessel. In addition, the flow of the antibody solution may be uneven due to the reasons such as wrinkles of the membrane, differences in hydrophilicity between the membrane and the plastic vessel, and stains on the surface of the vessel.

On the contrary, if the amount of antibody solution is very large, the membrane is fully immersed, and the unique effect of the CDR method disappears.

DISCLOSURE

Technical Problem

The present invention has been made to solve the above-mentioned conventional problems, and an object of the present invention is to provide an apparatus which allows blotting even with a small amount of antibody solution, allows a uniform antibody reaction to occur regardless of the membrane size, the placement direction of membrane, and the position within a membrane, and allows efficient antigen detection through a CDR antibody reaction.

Technical Solution

The CDR antibody reaction apparatus of the present invention for achieving the above object comprises: a chamber part in which an antibody solution is received and in which a blotting membrane that reacts with the antibody solution is disposed; and a spreader disposed on the blotting membrane in the chamber part, wherein the position of the spreader moves along the top of the blotting membrane.

Moreover, as the position of the spreader moves, the antibody solution may be evenly spread on the blotting membrane.

Furthermore, the antibody solution may be removed from the blotting membrane where the spreader is not located above.

In addition, the chamber part may further comprise a partition that partitions the inner space off.

Additionally, the chamber part may be provided with a plurality of protrusions formed on both sides of the inner bottom surface, and the plurality of protrusions may restrict the movements of the spreader and the mounted membrane by a predetermined distance.

Moreover, the chamber part may further comprise a pair of locking projections provided at the front and rear of at least one side and including a receiving groove in which the end of the spreader is received, and the spreader may be movable back and forth in the space between the receiving grooves.

Furthermore, the spreader may be located above the blotting membrane without making direct contact therewith.

In additional, the top of the chamber part may be provided with discharge grooves having a narrower width toward the front.

Additionally, there may be one or more spreaders.

Advantageous Effects

Since the CDR antibody reaction apparatus according to the present invention has an open top, it is easy to remove or add an antibody solution, which is suitable for process automation.

Moreover, since the CDR antibody reaction apparatus according to the present invention can control the movement of the antibody solution by means of the spreader, it allows blotting even with a small amount of antibody solution and allows a uniform antibody reaction to occur regardless of the membrane size, the placement direction of membrane, and the position within a membrane.

As a result, the CDR antibody reaction apparatus according to the present invention uses a small amount of antibody solution, allows efficient and strong antigen detection by applying the CDR principle, and allows even (uniform) blotting on the membrane.

DESCRIPTION OF DRAWINGS

FIG. 1 is a perspective view of a CDR antibody reaction apparatus according to the present invention.

FIG. 2 is a perspective view showing a chamber part of FIG. 1.

FIG. 3 is a perspective view showing the chamber part from which a partition of FIG. 2 is removed.

FIG. 4 shows the results of Western blot performed in a conventional (batch) method, in which a membrane is placed in a plastic vessel such as a business card case, and then an antibody solution in an amount sufficient to cover the membrane is added, in a conventional CDR (R-CDR) method which uses a rotating cylindrical tube, and performed on the CDR antibody reaction apparatus (S-CDR) of the present invention.

FIG. 5 shows the results of Western blot performed using the same amount of antigen with different antibody reaction times for the conventional (batch) method and the CDR antibody reaction apparatus (S-CDR) of the present invention.

FIG. 6 shows the results of dot Western blot performed using an antibody reaction apparatus in a conventional CDR (R-CDR) method and the CDR antibody reaction apparatus (S-CDR) of the present invention after applying the same amount of antigen in the form of dots to various places on the membrane.

FIGS. 7A and 7B show the results of dot Western blot performed using an antibody reaction apparatus in a conventional CDR (R-CDR) method and the CDR antibody reaction apparatus (S-CDR) the of present invention after intentionally crumpling the membrane so that the flow of the antibody solution is not consistent.

FIGS. 8 to 12 are perspective views of CDR antibody reaction apparatuses according to other embodiments of the present invention.

MODE FOR INVENTION

Hereinafter, preferred embodiments of the present invention will be described in detail with reference to the accompanying drawings. First, it should be noted that in adding reference numerals to the components of each drawing, the same components have the same reference numerals as much as possible even though they are shown in different drawings. Moreover, if it is determined that the subject matter of the present invention may be obscured, a detailed description thereof will be omitted. Furthermore, although preferred embodiments of the present invention will be described below, the technical idea of the present invention is not limited thereto and may be practiced by those skilled in the art.

Next, a CDR antibody reaction apparatus according to a preferred embodiment of the present invention will be described with reference to FIGS. 1 to 3.

Referring to FIG. 1, the CDR antibody reaction apparatus according to the present invention may comprise a chamber part 100 and a spreader 200. Here, the spreader 200 may be formed as a long "cylindrical" rod or may be configured in various other shapes such as a "sphere".

The chamber part 100 has a semi-cylindrical shape with a hollow bisected cylinder and an open top, in which an antibody solution can be received. The chamber part 100 may be made of, for example, an acrylic material, but is not limited thereto. The shape of the chamber part 100 may have a semi-cylindrical shape, as well as other shapes such as a hexahedral box with an open top.

In the case of the conventional cylindrical CDR reaction vessel, for each process, it is necessary that the cylindrical reaction vessel be removed from the rotating device and the lid be opened to add or remove a solution, which complicates the use of the reaction vessel and makes process automation difficult.

On the contrary, since the chamber part 100 of the present invention has an open top, it is easy to remove or add an antibody solution, which is suitable for process automation.

Moreover, the chamber part 100 may be provided with a blotting membrane 10 that reacts with the antibody solution. Here, in the blotting membrane 10, an antigen which reacts with the antibody solution can be immobilized, and the immobilized antigen may be disposed to face the open top of the chamber part 100.

In addition, the chamber part 100 may further comprise a partition 110 that partitions the inner space off.

In this case, the position of the partition 110 may vary depending on the length of the blotting membrane 10 used, and a plurality of partitions may be provided.

For example, when the length of the blotting membrane 10 used is short as shown in FIG. 2, the partition 110 may be provided to divide the inner space of the chamber part 100 into two spaces.

On the contrary, when the length of the blotting membrane 10 is long as shown in FIG. 3, the partition 110 may be removed from the chamber part 100.

Referring back to FIG. 1, the spreader 200 may be disposed on the blotting membrane 10 in the chamber part 100. The spreader 200 is not directly fixed to the chamber part 100, but has a circular tube shape to move back and forth while rolling as the chamber part 100 is tilted Referring to FIGS. 1 to 3, the chamber part 100 has a plurality of protrusions 120 formed at regular intervals on both sides of the inner bottom surface to restrict the movements of the spreader 200 and the mounted membrane by a certain distance.

Moreover, in order to prevent the spreader 200 from being separated from the chamber part 100 when the chamber part 100 is tilted back and forth, it is preferable that the plurality of protrusions 120 extend upward by a predetermined height.

Referring to FIGS. 2 and 3, the chamber part 100 may further comprise locking projections 130. A pair of locking projections 130 may be provided at the front and rear of at least one side and including a receiving groove 131 in which the end of the spreader 200 is received. Here, the at least one side may be one side S1, the other side S2 of the chamber part 100, or the partition 110 described above.

As the locking projections 130 are provided in this way, the spreader 200 is movable back and forth in the space between the receiving grooves formed in the pair of locking projections 130, and since the spreader 200 moves in a state where the outside is surrounded by the locking projections 130, it is possible to more reliably prevent the spreader 200 from being separated.

Meanwhile, the top of the chamber part 100 is provided with discharge grooves 140 having a narrower width toward the front, which make it possible for the solution inside the chamber part 100 to be easily discharged through a vessel C disposed on the bottom.

Moreover, although not shown in detail, when the spreader 200 directly contacts the blotting membrane 10, it is highly likely to damage the membrane, and thus slightly projecting portions 210 may be formed at both ends (as shown in FIG. 8), which allow the spreader to be disposed at short intervals from the blotting membrane 10. Therefore, the spreader is located at short intervals on the top of the membrane, and the antibody solution is collected in the gap between the spreader and the membrane and at the periphery of the spreader.

Next, the operation of the CDR antibody reaction apparatus according to a preferred embodiment of the present invention will be described.

Referring to FIGS. 1 to 3, the blotting membrane 10 is disposed in the semi-cylindrical chamber part 100 with an open top, and the antibody solution which reacts with an antigen immobilized on the blotting membrane 10 is introduced into the chamber part 100. Here, the antibody solution may be added in an amount sufficient to fill the bottom of the spreader 200 or in a greater amount.

In this state, when a driving force is transmitted from a driving unit (not shown) connected to the chamber part 100, the chamber part 100 may be tilted back and forth based on a longitudinal axis a as shown by the arrows in FIGS. 2 and 3. As an example, the chamber part 100 may be tilted in a manner that the front tilted downward in FIG. 1(a) moves upward as shown in FIG. 1(b), or in a manner that the front of the chamber part 100 moves from the top to the bottom.

As the chamber part 100 is tilted back and forth in this way, the spreader 200 disposed on the blotting membrane 10 can move back and forth over the chamber part 100.

This movement of the spreader 200 allows the antibody solution collected at the bottom and periphery of the spreader 200 to move on the blotting membrane 10. That is, the spreader 200 moves in such a manner that the antibody solution is evenly spread on and removed from the blotting membrane 10, and thus it is possible to increase the antigen-antibody binding efficiency by implementing the CDR antibody reaction principle.

Referring to FIG. 4, the results of Western blot performed in a conventional (batch) method, in which the membrane is placed in a plastic vessel such as a business card case, and then an antibody solution in an amount sufficient to cover the membrane is added, in a conventional CDR (R-CDR) method which uses a rotating cylindrical tube, and performed on the CDR antibody reaction apparatus (S-CDR) of the present invention were analyzed.

As a result of comparing the performances of the antibody reactions based on the intensity of the signal according to the amount of the sample when the antigen is GAPDH or Beta Actin, it was found that the intensity of the signal was higher when Western blot was performed using the CDR antibody reaction apparatus of the present invention, indicating a higher performance of the antibody reaction than that of the conventional methods. As such, the present invention has an advantage in that an excellent signal quality can be obtained with high sensitivity compared to the conventional methods.

Referring to FIG. 5, the results of Western blot using the same amount of antigen with different antibody reaction times for the conventional (batch) method and the CDR antibody reaction apparatus (S-CDR) of the present invention were analyzed.

That is, antigen detection can occur quickly and effectively, thereby reducing antigen reaction time. The present invention increases the efficiency of the antibody reaction.

Moreover, the CDR antibody reaction apparatus according to the present invention can control the movement of the antibody solution by means of the spreader 200, which allows blotting even with a small amount of antibody solution (0.25 ml to 1.0 ml in the case of mini-blot), and allows a uniform antibody reaction to occur regardless of the membrane size, the placement direction of membrane, and the position within a membrane.

Referring to FIG. 6, the results of dot Western blot obtained by performing the CDR antibody reaction in a method without a spreader (R-CDR) and in a method with the spreader (S-CDR) after applying the same amount of antigen in the form of dots to various places on the membrane were analyzed.

Here, the values measured at the dots of each membrane were averaged for each column, and the standard error was calculated.

The amount of antibody solution used was 2 ml to 0.25 ml, and according to the present invention, it is possible to reduce the amount of antibody used and to obtain uniform results.

Specifically, (1) the signals at the respective dots should theoretically be the same. In the case of the S-CDR method with the spreader, the signal values were more uniform (compared the standard errors of the analysis values). (2) When using the spreader, uniform signals were obtained up to 0.25 ml; however, in the case of the R-CDR method without the spreader, when using the antibodies in amounts of 0.5 and 0.25 ml, the antibody reaction did not occur well in some areas.

Figure 7B:
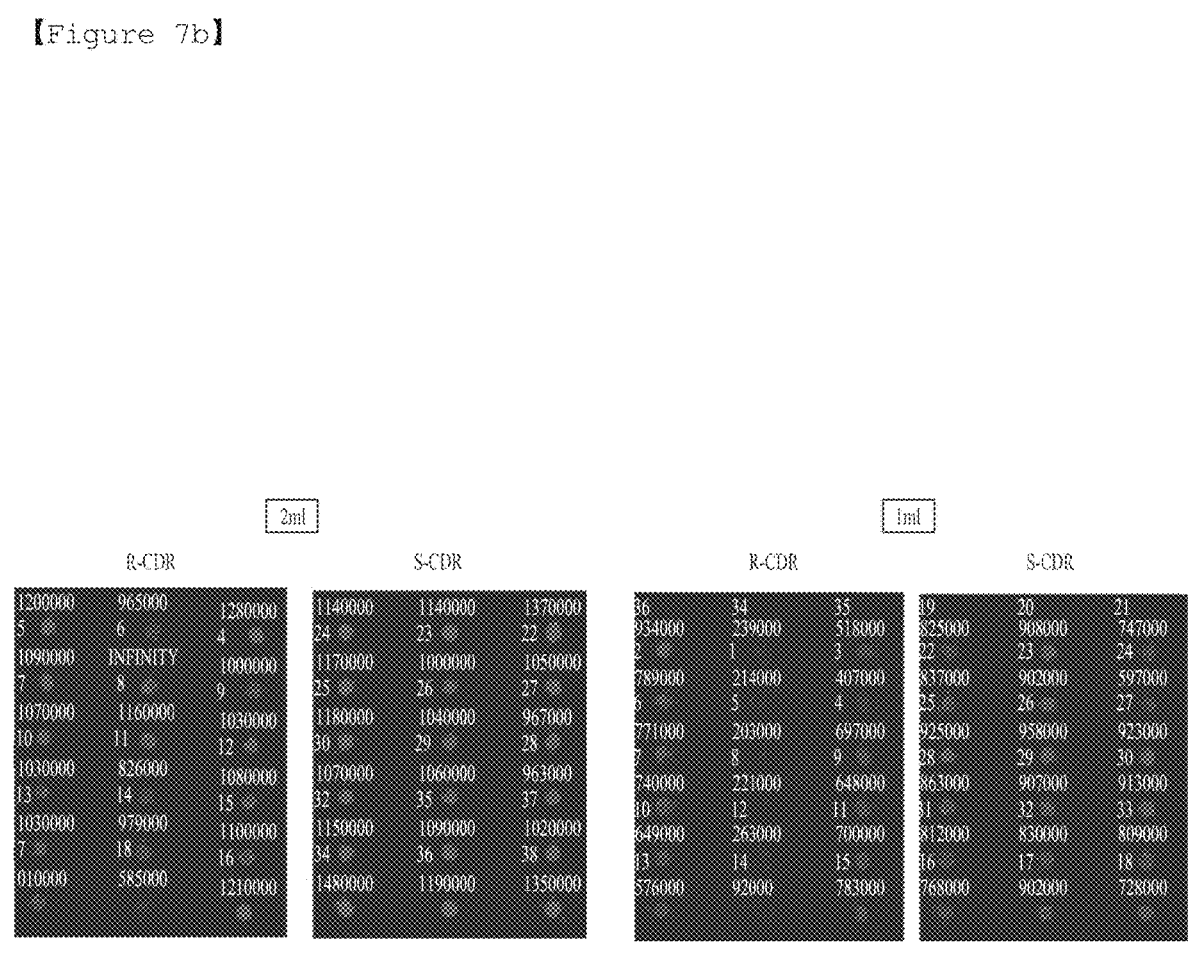

Referring to FIGS. 7A and 7B, the results of dot Western blot performed using an antibody reaction apparatus in a conventional CDR (R-CDR) method and the CDR antibody reaction apparatus (S-CDR) of the present invention after intentionally crumpling the membrane so that the flow of the antibody solution is not consistent were analyzed.

The purpose of the experiment is to determine whether the spreader can promote the movement of the antibody solution to obtain a uniform antibody-antigen reaction even when the membrane is folded or damaged during the experiment.

As a result, in the case of R-CDR without the spreader, the reaction did not occur well in some areas or the values were not uniform. However, the present invention produced uniform results.

Next, CDR antibody reaction apparatuses according to other embodiments of the present invention will be described.

FIGS. 8 to 12 are perspective views of CDR antibody reaction apparatuses according to other embodiments of the present invention.

As shown in FIG. 8, a CDR antibody reaction apparatus according to another embodiment of the present invention comprises a chamber part 100a and a spreader 200b.

Here, two or more spreaders 200b are provided to allow the antibody solution to be restricted within the space between the spreaders 200b, leading to a more precise movement control.

In the embodiment of FIG. 8, two or more spreaders 200b are provided only, and the configuration and operation are the same as those of FIG. 1.

As shown in FIG. 9, a CDR antibody reaction apparatus according to still another embodiment of the present invention comprises: a rectangular parallelepiped chamber part 100b with an open top, in which the antibody solution is received; and a spherical spreader 200b.

Accordingly, the spherical spreader 200b moves by the movement of the chamber 100b.

As shown in FIG. 10, a CDR antibody reaction apparatus according to further another embodiment of the present invention comprises: a rectangular parallelepiped chamber part 100c with an open top, in which the antibody solution is received; a cylindrical spreader 200c; and a cover 300c for covering the open top of the chamber part 100c.

As shown in FIG. 11, a CDR antibody reaction apparatus according to still further another embodiment of the present invention comprises: a chamber part 100*d* having a semi-cylindrical shape with a hollow bisected cylinder and an open top, in which the antibody solution is received; and a spreader 200*d* having a plate shape and is fixed so as not to move.

As a result, as the chamber 100*d* moves, the relative position of the spreader 200*d* also moves.

As shown in FIG. 12, a CDR antibody reaction apparatus according to a further embodiment of the present invention comprises: a rectangular parallelepiped chamber part 100*e* with an open top, in which the antibody solution is received; a spreader 200*e* composed of a cylindrical rod and made of iron; and a magnet 300*e* for moving the spreader 200*e*.

As mentioned above, the preferred embodiments of the present invention have been described in detail; however, the technical scope of the present invention is not limited to the above-described embodiments and should be interpreted by the claims. Those skilled in the art should appreciate that many modifications and variations are possible without departing from the scope of the present invention.

The invention claimed is:

1. A cyclic draining and replenishing (CDR) antibody reaction apparatus comprising:
   a chamber part having a front, a back, sides, and a bottom with an inner blotting membrane-mounting surface, the chamber configured for receiving an antibody solution; and
   a spreader having two ends, each end having a projecting portion formed thereon, the spreader disposed in the chamber above the blotting membrane mounting surface and movable back and forth thereover at a distance, defined by the projecting portions, sufficient to prevent the spreader from directly contacting a top surface of a blotting membrane when mounted on the blotting membrane-mounting surface in operation of the device.

2. The CDR antibody reaction apparatus according to claim 1, wherein as the position of the spreader moves, the antibody solution is evenly spread on the blotting membrane.

3. The CDR antibody reaction apparatus according to claim 1, wherein the antibody solution is removed from the blotting membrane where the spreader is not located above.

4. The CDR antibody reaction apparatus according to claim 1, wherein the chamber part further comprises a partition that partitions the inner space off.

5. The CDR antibody reaction apparatus according to claim 4, wherein there is a plurality of spreaders.

6. The CDR antibody reaction apparatus according to claim 1, wherein the chamber part is provided with a plurality of protrusions formed on both sides of the inner bottom surface, and the plurality of protrusions restrict the movements of the spreader and the mounted membrane by a predetermined distance.

7. The CDR antibody reaction apparatus according to claim 1, wherein the chamber part further comprises a pair of locking projections provided at the front and rear of at least one side and including a receiving groove in which the end of the spreader is received, and wherein the spreader is movable back and forth in the space between the receiving grooves.

8. The CDR antibody reaction apparatus according to claim 1, wherein a top of the chamber part is provided with discharge grooves having a narrower width toward the front.

9. The CDR antibody reaction apparatus according to claim 1, wherein there is a plurality of spreaders.

* * * * *